(12) United States Patent
DeBlock

(10) Patent No.: US 10,149,447 B2
(45) Date of Patent: Dec. 11, 2018

(54) METHODS AND MEANS FOR DETERMINING PLANT CHARACTERISTICS

(71) Applicant: Bayer CropScience NV, Diegem (BE)

(72) Inventor: Marc DeBlock, Merelbeke (BE)

( * ) Notice: Subject to any disclaimer, the term of this patent is extended or adjusted under 35 U.S.C. 154(b) by 28 days.

(21) Appl. No.: 14/888,553

(22) PCT Filed: May 15, 2014

(86) PCT No.: PCT/EP2014/059915
§ 371 (c)(1),
(2) Date: Nov. 2, 2015

(87) PCT Pub. No.: WO2014/184278
PCT Pub. Date: Nov. 20, 2014

(65) Prior Publication Data
US 2016/0081285 A1     Mar. 24, 2016

(30) Foreign Application Priority Data

May 17, 2013 (EP) ..................................... 13168180

(51) Int. Cl.
*A01H 1/04* (2006.01)
*G01N 33/00* (2006.01)
*G01N 33/82* (2006.01)

(52) U.S. Cl.
CPC ........... *A01H 1/04* (2013.01); *G01N 33/0098* (2013.01); *G01N 33/82* (2013.01)

(58) Field of Classification Search
None
See application file for complete search history.

(56) References Cited

U.S. PATENT DOCUMENTS

2008/0209584 A1\*  8/2008  Levy .......................... A01H 5/08
800/260

FOREIGN PATENT DOCUMENTS

| WO | 06267 | 2/1997 |
| WO | 066972 A2 | 8/2002 |
| WO | 000466 A1 | 1/2011 |

OTHER PUBLICATIONS

De la Torre 2008 The Scientific World Journal 8:1197-1209.*
Grbic et al 1995 The Plant Journal 8:595-602.*
Machado De Carvalho et al 1997 New Phytol. 136:153-161.*
Barth, Carina, et al., The Timing of Senescence and Response to Pathogens Is Altered in the Ascorbate-Deficient *Arabidopsis* Mutant vitamin c-11, Plant Physiology, Apr. 2004, vol. 134, pp. 1784-1792.
Barth, Carina, et al., The role of ascorbic acid in the control of flowering time and the onset of senescence, Journal of Experiemental Botany, 2006, vol. 57, No. 8, pp. 1657-1665.

Bradley, Daniel W., et al., Vitamin C in Plasma: A Comparative Study of the Vitamin Stabilized With Trichloroacetic Acid or Metaphosphoric Acid and the Effects of Storage AT-7o,-zoo, 4', and 25' on the Stabilized Vitamin, Clinica Chimica Acta, 1973, vol. 44, pp. 47-52.
Conklin, P. L., et al., Ascorbic acid, a familiar small molecule intertwined in the response of plants to ozone, pathogens, and the onset of senescence, Plant, Cell and Environment, 2004, vol. 27, pp. 959-970.
Concetta De Pinto, Maria , et al., Hydrogen peroxide, nitric oxide and cytosolic ascorbate peroxidase at the crossroad between defence and cell death, The Plant Journal, 2006, vol. 48, pp. 784-795.
Duncan, David R., et al., Proline Is Not the Primary Determinant of Chilling Tolerance Induced by Mannitol or Abscisic Acid in Regenerable Maize Callus Cultures1, Plant Physiol., 1991, vol. 95, pp. 1284-1287.
Gallie, Daniel R. , ソ-Ascorbic Acid: A Multifunctional Molecule Supporting Plant Growth and Development, Hindawi Publishing Corporation, 2013.
Gao, Qian , et al., Ultraviolet-B-induced oxidative stress and antioxidant defense system responses in ascorbate-deficient vtc1 mutants of *Arabidopsis thaliana*, Journal of Plant Physiology, 2008, vol. 165, pp. 138-148.
Gest, Noe, et al., Ascorbate as seen through plant evolution: the rise of a successful molecule?, Journal of Experimental Botany, 2013, vol. 64, No. 1, pp. 33-53.
Haubena, Miriam, et al., Energy use efficiency is characterized by an epigenetic component that can be directed through artificial selection to increase yield, PNAS, Nov. 24, 2009, vol. 106, No. 47, pp. 20109-20114.
Ishikawa, Masaya , et al., Comparison of viability tests for assessing cross-adaptation to freezing, heat and salt stresses induced by abscisic acid in bromegrass (Bromus inermis Leyss) suspension cultured cells, Plant Science, 1995, vol. 107, pp. 83-93.
Larkindale, Jane, et al., Heat Stress Phenotypes of *Arabidopsis* Mutants Implicate Multiple Signaling Pathways in the Acquisition of Therrnotolerance1[w], Plant Physiology, Jun. 2005, vol. 138, pp. 882-897.
Lichtentaler and Miehé, Fluorescence imaging as a diagnostic tool for plant stress, Elsevier Science Ltd, Aug. 1997, vol. 2, No. 8.
Muller-Moule, Patricia, et al, Ascorbate-Deficient Mutants of *Arabidopsis* Grow in High Light Despite Chronic Photooxidative Stress1, Plant Physiology, Mar. 2004, vol. 134, pp. 1163-1172.
Pignocch I, Cristina et al., Apoplastic ascorbate metabolism and its role in the regulation of cell signalling, Current Opinion in Plant Biology, 2003, vol. 6, pp. 379-389.
Pineau, Bernard, et al., L-Galactono-1,4-lactone Dehydrogenase Is Required for the Accumulation of Plant Respiratory Complex I, The Journal of Biological Chemistry, Nov. 21, 2008, vol. 283, No. 47, pp. 32500-32505.
Popov, A.S., et al., A Rapid viability Assay for Plant Shoot Apical meristems, Russian Journal of Plant Physiology, 1996, vol. 43, No. 2, pp. 263-269.
Szarka, Andras, et al., Dehydroascorbate reduction in plant mitochondria is coupled to the respiratory electron transfer chain, Physiologia Plantarum, 2007, vol. 129:, pp. 225-232.
Talla, Saikrishna, et al., Ascorbic acid is a key participant during the interactions between chloroplasts and mitochondria to optimize photosynthesis and protect against photoinhibition, J Bioscience, Mar. 2011, vol. 36(1), pp. 163-173.

(Continued)

*Primary Examiner* — Brent T Page

(57) ABSTRACT

The invention provides methods to determine the ascorbate profile value for plant lines and to use these values in the identification of the better performing plant lines, without having to resort to extensive field trialing.

14 Claims, 4 Drawing Sheets

(56) References Cited

OTHER PUBLICATIONS

Towill, Leigh E., et al., Studies on the reduction of 2,3,S-triphenyrtetrazolium chloride as a viatrility assay for plant tissue cultures, 1975, Can. J. Bot. 53: 1097-1102.

Wojtyla, Lukasz, et al., A comparative study of water distribution, free radical production and activation of antioxidative metabolism in germinating pea seeds, Journal of Plant Physiology, 2006, vol. 163, pp. 1207-1220.

Smirnoff, Nicholas, et al., Ascorbic Acid in Plants: Biosynthesis and Function, Critical Review in Biochem. Mol. Biol., 2000, vol. 35, pp. 291-314.

Lichtenthaler, Hartmut K., Vegetation Stress: An Introduction to the Stress Concept in Plants, Journal of Plant Physiol. 1996, vol. 148. pp. 4-14.

\* cited by examiner

METHODS AND MEANS FOR DETERMINING PLANT CHARACTERISTICS

CROSS-REFERENCE TO RELATED APPLICATIONS

This application is a § 371 U.S. National Stage of International Application No. PCT/EP14/059915 filed May 15, 2014, which claims the benefit of the EP Patent Application Serial No. 13168180.1, filed May 17, 2013, the contents of which are herein incorporated by reference in their entirety.

FIELD OF THE INVENTION

The present invention relates to the field of agriculture, including horticulture, olericulture, viticulture or arboriculture. More specifically, methods and means are provided for predicting the plant line characteristics such as yield potential of a plant line, or shelf life of the plants or harvested parts thereof, on the basis of the ascorbate profile of fully developed plant parts of relatively young sample plants. Such sample plants may be grown in growth chambers or greenhouses.

BACKGROUND

Vitamin C (L-ascorbic acid or L-ascorbate) is an essential co-factor for enzymes catalyzing numerous biochemical reactions including hydroxylation, as well as a primary antioxidant in both plants and animals. In plants, L-ascorbate has been implicated in processes including growth (Pignocchi and Foyer, 2003, *Curr. Opin. Plant Biol.* 6, 379-389) programmed cell death (de Pinto et al., 2006, *Plant J.* 48, 784-795), pathogen responses (Barth et al., 2004, *Plant Physiol.* 134, 1784-1792), hormone responses, flowering and senescence (Barth et al., 2006, *J. Exp. Bot.* 57, 1657-1665), as well as protection against environmental stresses including ozone (Conklin and Barth, 2004, *Plant Cell Environ.* 27, 959-970), UV radiation (Gao and Zhang, 2008, *J. Plant Physiol.* 165, 138-148), high temperatures (Larkindale et al., 2005, *Plant Physiol.* 138, 882-897) and high light intensity (Muller-Moulé et al. 2004, *Plant Physiol.* 134, 1163-1172).

The concentration in ascorbate in plants and plant cells is determined, on the one hand by de novo ascorbate synthesis as well as regeneration of ascorbate from its oxidized forms, and on the other hand, by consumption of ascorbate in the detoxification of reactive oxygen species (ROS) and hydrogenperoxide ($H_2O_2$) generated through the respiration process or in response to stress conditions.

Synthesis of vitamin C in plants has only been relatively recently elucidated and is referred to as the L-galactose pathway or Smirnoff-Wheeler pathway (Smirnoff et al. 2000, *Crit. Rev. Biochem. Mol. Biol.* 35, 291-314). The first six steps of the L-galactose pathway synthesize activated nucleotide sugars that are also precursors of cell wall polysaccharides and glycoproteins. The committed pathway to L-ascorbate biosynthesis then consists of the sequential conversion of GDP-L-galactose into L-galactose-1-P, L-galactose, L-galactono-1,4-lactone and L-ascorbate. The enzyme catalyzing the last step reaction, L-galactono-1,4 lactone dehydrogenase, is associated with mitochondrial NADH-ubiquinone oxidoreductase (complex I) (Pineau et al., 2008, *J. Biol. Chem.* 283, 32500-32505).

Ascorbate becomes rapidly oxidized to monodehydroascorbate via reactions involving oxidative species (including reduction of $H_2O_2$ through ascorbate peroxidase). Monodehydroascorbate is further oxidized spontaneously to dehydroascorbate. To prevent the degradation of dehydroascorbate via ring opening, dehydroascorbate must be rapidly recycled to avoid depletion of the ascorbate pools.

Ascorbate recycling also occurs in the plant mitochondria. Dehydroascorbate can be reduced to ascorbate by two main mechanisms. Electrons can be provided by small electron carriers, such as glutathione or lipoic acid, through the action of dehydroascorbate reductase, or by the respiratory electron transfer chain. Using substrates and inhibitors of the respiratory electron transfer chain, the site of dehydroascorbate reduction was localized to complex II (Szarka et al. 2007, *Physiologia Plantarum* 129: 225-232).

Talla et al. (2011, *J. BioSci* 36, 163-173) suggest that ascorbic acid is a key participant during the interactions between chloroplasts and mitochondria to optimize photosynthesis and protect against photoinhibition.

The currently used methods to determine the yield potential of plant lines (such as plant lines resulting from conventional breeding activities, and/or plant lines with an engineered trait, be it through transgenesis, mutagenesis or other means) consists in performing field trials at different locations, preferably under different conditions. A disadvantage of field trials for crop plants, is that, at best, only two experiments can be done each year. Even when field trials are planned very well and deliver the appropriate data, this time constraint interferes with the continuity of the projects and slows down the progress.

A number of assays (mainly qualitative) have been described for use in plant tissue culture to study the effect of various stresses on the survival of cells or tissues (Towill and Mazur, 1975; Chen et al. 1982, Duncan and Widholm 1990, Stepan-Sarkissian and Grey, 1990; Upadhyaya and Caldwell, 1993; Enikeev et al., 1995; Ishikawa et al., 1995; Popov and Vysotskaya, 1996). These are actually "viability" assays which do not measure the yield potential of plants.

Chlorophyll fluorescence and fluorescence imaging may also be used to study the influences of stress conditions on whole plants (Lichtenthaler, 1996; Lichtentaler and Mieké, 1997). Although these assays provide some data on the tolerance of the plant lines to certain stresses, they cannot be used to measure yield potential.

WO 97/06267 describe the use of PARP inhibitors to improve the transformation (qualitatively or quantitatively) of eukaryotic cells, particularly plant cells. Also described is a method for assessing the agronomical fitness of plants or plant material by measuring the electron flow in the mitochondrial electron transport chain.

WO 2002/066972 provides methods and means for determining parent inbred plant lines with good combining ability, for determining good combinations of parent inbred plant lines capable of yielding hybrid lines with high heterosis, and further for determining the agronomical performance of different plant lines, which can be performed in vitro by determining the electron flow in the mitochondria under control and stress conditions.

There remains however a need to improve the prediction methods described in the art to arrive at an improved method allowing to predict important plant characteristics, such as yield potential or increased shelf life, in an early stage of plant development, with sufficient accuracy, without having to resort to field trials. Such methods would represent an extra tool to rapidly identify plant lines of high interest in breeding programs, allowing to discard non-promising lines rapidly and could result in a significant gain of time and resources.

The current invention provides such methods as described in the various embodiments and claims disclosed herein.

SUMMARY OF THE INVENTION

In one embodiment of the invention, a method is provided for determining the ascorbate profile value of a plant line comprising the steps of
  a. growing several seedlings of the plant line for a time sufficient to generate a population of seedlings wherein at least one plant part does not develop any further, optionally starts to demonstrate symptoms of senescence;
  b. optionally, applying moderate stress, such as moderate drought stress, prior to the step of determining the weight and ascorbate concentration in the individual plant parts;
  c. determining the weight of the individual plant parts and measuring the concentration of ascorbate in the individual plant parts;
  d. plotting the concentration of ascorbate versus the weight determined for each individual plant to obtain a collection of data points;
  e. performing regression analysis on the data points to obtain a linear regression curve; and
  f. determining the slope of the linear regression curve, which corresponds to the ascorbate profile value of the plant line.

In one embodiment, the plant part which does not develop any further is a cotyledon or an epicotyl; in another embodiment the plant part which does not develop any further is the first or second developing true leaf. The ascorbate concentration can be measured in any conventional way, such as by specific light (530 nm) adsorption of the dinitrophenylhydrazine derivative of oxidized ascorbic acid, or by measuring the reduction of yellow molybdophosphoric acid to phosphomolybdenum blue by ascorbic acid reflectometrically. The methods may be applied to any plant, including oilseed rape, lettuce, tobacco, cotton, corn, rice, wheat, vegetable plants, carrot, cucumber, leek, pea, melon, potato, tomato, sorghum, rye, oat, sugarcane, peanut, flax, bean, sugarbeets, soya, sunflower, ornamental plants. The methods are particularly suited for *Brassica* oilseed rape plant lines, wheat lines, cotton lines, rice lines, corn lines or lettuce plant lines including hybrids.

In another embodiment, the invention provides a method for determining the relative ascorbate profile value of a test plant line compared to a reference plant line grown comprising the steps of determining the ascorbate profile value for a test plant line and for a reference plant line grown under similar conditions according to the methods of the invention and dividing the ascorbate profile value of the test plant line by the ascorbate profile value of the reference plant line to obtain the relative ascorbate profile value.

In yet another embodiment, the invention provides a method for identifying the better performing plant lines from a population of plant lines, such as a breeding population, comprising the steps of
  a. providing a population of plant lines;
  b. determining the relative ascorbate profile value for each of the plant lines of the population compared to a reference plant line by the method according to the invention; and
  c. selecting one or more plant lines with the highest relative ascorbate profile values.

The invention also provides a method for predicting the relative yield potential of a plant line comprising the step of determining the relative ascorbate profile value for the plant line compared to a reference plant line with known yield potential by the method according to the invention, wherein the more the relative ascorbate profile value is larger than 1, the more the yield potential of the plant line will be larger than the yield potential of the reference line.

It is also an object of the invention to provide a method for predicting the relative shelf life of a plant line or parts of the plant comprising the step of determining the relative ascorbate profile value for the plant line compared to a reference plant line with known shelf life by the methods according to the invention, wherein the more the relative ascorbate profile value is larger than 1, the more the shelf life of the plant line or part thereof will be longer than the shelf life of the reference line or part thereof.

Also provided is a method for determining the yield potential of plant lines in a population of plant lines comprising the steps of
  a. providing a population of plant lines;
  b. determining the relative ascorbate profile value for each of the plant lines of the population compared to a reference plant line by the methods according to the invention;
  c. determining the yield potential of selected plant lines by conventional field trials; and optionally selecting one or more plant lines with the highest relative ascorbate profile values and/or highest yield potential determined by field trial.

The invention further provides a method for determining the shelf life of plant lines in a population of plant lines comprising the steps of
  a. providing a population of plant lines;
  b. determining the relative ascorbate profile value for each of the plant lines of the population compared to a reference plant line by the methods according to the invention;
  c. selecting one or more plant lines with the highest relative ascorbate profile values;
  d. determining the shelf life of selected plant lines or parts thereof by growing plants and performing conventional shelf life trials; and optionally selecting one or more plant lines with the highest relative ascorbate profile values and/or highest shelf life determined by trial.

It is also an object of the invention to provide a method for breeding plants comprising the step of
  a. generating a breeding population of plant lines;
  b. determining the relative ascorbate profile value for each of the plant lines of the population compared to a reference plant line by the methods according to the invention;
  c. selecting one or more plant lines with the highest relative ascorbate profile value(s);
  d. crossing the selected plant lines with other plants to generate a further breeding population; and
  e. optionally reiterating the process through steps b to d.

The invention also provides a method for selecting parental lines in hybrid plant production comprising the steps of
  a. providing a population of at least two parental plant lines;
  b. crossing different combinations of parental plant lines selected from the population to generate hybrid plant lines;
  c. determining the relative ascorbate profile value for the hybrid plant lines according to the methods of the invention;
  d. selecting parental lines which yield hybrid plant lines with the highest ascorbate profile value.

The invention also provides plant lines with a relative ascorbate profile value of more than one when compared to the best reference plant lines of those plant species or *Brassica* plant with an ascorbate profile value of more than 330.

DETAILED DESCRIPTION OF SEVERAL EMBODIMENTS OF THE INVENTION

Figure 1:
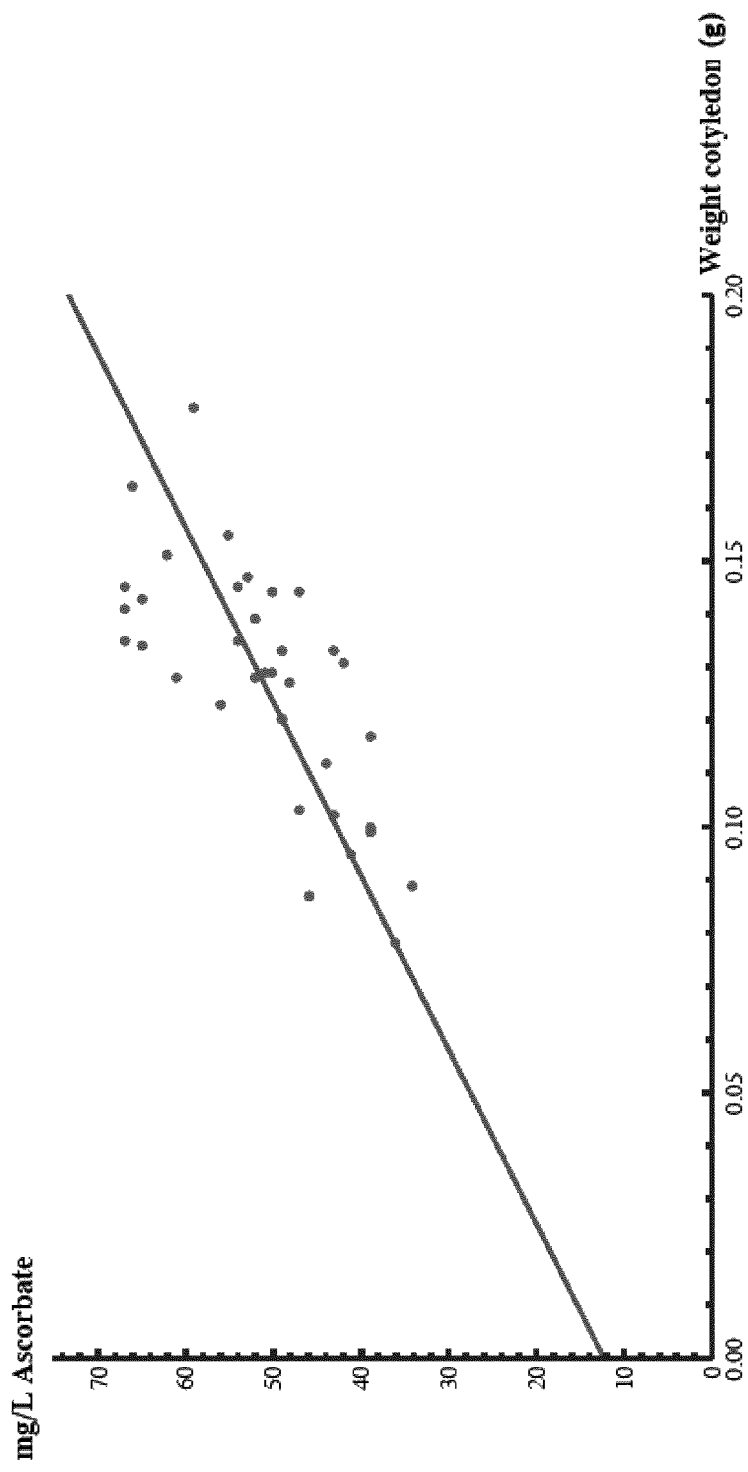
FIG. 1 is a schematic representation of a data plot graph for ascorbate concentrations versus weights of individual cotyledons of a plant line and regression curve. The slope of the regression curve represents the ascorbate profile value of the plant line. X-axis: weight of the cotyledon in gram. Y-axis: ascorbate concentration in mg/L.
Figure 2:
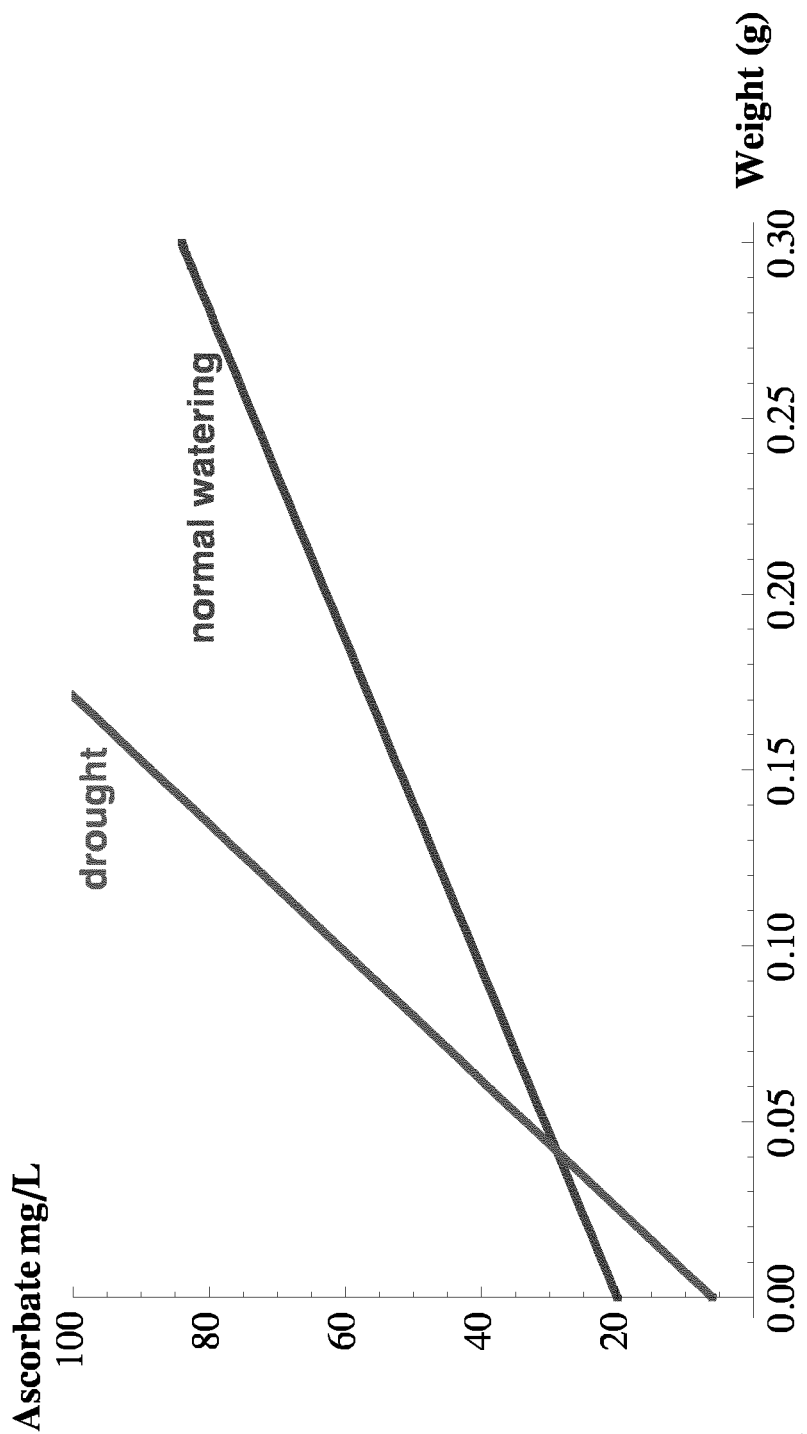
FIG. 2 is a schematic representation of the influence of moderate drought stress on the determined ascorbate profile value of the plant line. X-axis: weight of the cotyledon in gram. Y-axis: ascorbate concentration in mg/L.

The current invention is based on the observed close correlation between the slope of the linear regression curve obtained by regression analysis of data points consisting of the ascorbate concentration (on the Y-axis) versus the weight of individual cotyledons (on the X-axis) in a population of seedlings, and the important characteristics of the plant line of which the seedlings are derived from, including yield potential and/or shelf life. This correlation can be applied e.g. to identify and/or select the best performing plant lines from a population of plant lines, such as a breeding population of plant lines, prior to having performed any field trials.

Thus, the invention provides a method for determining the "ascorbate profile value" of a plant line comprising the steps of growing several seedlings of said plant line for a time sufficient to generate a population of seedlings wherein at least one plant part does not develop any further. The weight of the individual plant parts are determined, as well as the concentration of ascorbate in those individual plant parts. Next a regression analysis is performed on the data points the coordinates of which consist of the concentration of ascorbate (abscis) and the weight (ordinate) determined for each individual plant to obtain a linear regression curve. The slope of the linear regression curve (i.e. the value "a" in the formula $y=ax+b$ is referred to as the "ascorbate profile value" of the plant line.

In principle, any plant tissue or organ which has a determined growth can be used. The seedlings should be grown for a time period sufficient for the chosen plant tissue or organ to have reached its full growth potential, whereby in principle the chosen plant tissue or organ is not developing any further (other than senescing). Preferred material to perform the analysis on, is material from young seedlings. This material has a shorter growth period and the ascorbate concentration is less dependent on extrinsic factors which may have an influence. Moreover, material of young seedlings is usually smaller and the whole tissue or organ can be used, thereby reducing any fluctuation in ascorbate concentration within the plant tissue or organ. Advantageously, young seedlings consume less resources and space to grow them, and the methods according to the invention are thus appropriate for a higher throughput.

Preferably, the analysis is performed on cotyledons of young seedlings grown for a period of time sufficient to obtain a population wherein the young plants have smaller and larger cotyledons, and wherein some cotyledons may even demonstrate first symptoms of senescence as determined by biochemical assay (onset of protein degradation) or by molecular assay (induction of early-induced SAG gene expression). It is however important that the cotyledons do not yet show visible symptoms of senescence. For *Brassica* plants, the seedlings are preferably grown for 10 to 15 days, preferably about 12 days. In monocotyledonous plants, the coleoptyl may be used for the analysis according to the methods of the invention. However, where the coleoptyl is too small, such as e.g. in wheat plants, the analysis may also be performed on the first true leaf to emerge, after it has been fully grown. For wheat, seedlings are preferably grown for 10 to 15 days, preferably about 12 days. For rice, seedlings are preferably grown for 14 to 20 days, preferably about 17 days (for rice, the analysis is preferably performed on the second true leaf).

The ascorbate profile value can also be correlated with the shelf life of plants, or harvested parts thereof. For lettuce e.g. the value may allow prediction of the shelf life of the harvest lettuce heads, while for tomato, the shelf life of harvested tomato fruits may be predicted.

It should also be emphasized that the correlation is between yield potential of a plant line and the ascorbate profile value, but not with the ascorbate content or ascorbate concentration. Table 1 provides values determined for ascorbate concentration, ascorbate content and ascorbate profile value for 4 *B. napus* plant lines. It will be immediately clear that the plant line (d) with the highest ascorbate profile value, and thus with highest yield potential is neither the plant line with the highest ascorbate concentration (plant line (a)) nor the plant with the highest ascorbate content in the cotyledons (plant line (b)).

TABLE 1

| Plant line | Ascorbate profile value | Ascorbate concentration (mg/L) | Ascorbate content (mg per cotelydon) |
| --- | --- | --- | --- |
| a | 298 | 7.0 | 52 |
| b | 305 | 6.5 | 54 |
| c | 340 | 6.4 | 51 |
| d | 351 | 6.8 | 50 |

It has also been observed that applying moderate stresses at the end of the growth period accentuates the intrinsic differences between various plant lines, or hybrids. Moderate stresses which could be applied include cold, heat, watering with a solution containing salicylic acid derivatives, exposure to high light conditions etc. A preferred and easy to apply stress condition is drought stress. The seedlings are normally watered every other day, except for the last time prior to harvesting. In this way, the plants have received no water for about 3 to about 4 days prior to harvesting.

Although not intending to limit the invention to a particular mode of action, it is thought that ascorbate concentration in a population is determined by mitochondrial activity (both ascorbate synthesis and regeneration occur in mitochondria) which in turn is determined by the state of a leaf (developmental stage, senescence and stress). Large cotyledons that have still a high ascorbate concentration results in greater longevity. Under stress conditions, ascorbate production is increased. Senescing cotyledons will have no or only a small increase of ascorbate under stress conditions. The ascorbate profile value as defined above, reflects the dynamic state of the population and the possibility to adapt under stress conditions. The steeper the slope (i.e. the ascorbate profile value), the higher the ascorbate production and regeneration, and the slower the senescence, each reflecting the higher vigor of the plant population.

Determination of the ascorbic acid content (and calculation of the ascorbic acid concentration) can be performed using any conventional assay. For example, ascorbic acid content in plant extracts may be determined using the dinitrophenylhydrazine method essentially as described by Daniel et al. 1973 (Clinica Chimica Acta, 44, 47-52). The ascorbic acid in a given sample is converted to dehydroascorbic acid by an oxidizing agent and the dehydroascorbic acid is derivatized with dinitrophenylhydrazine. The vitamin C concentration can be determined by the specific light (530 nm) adsorption of the dinitrophenylhydrazine derivative. An assay kit to perform these reactions can be purchased e.g. from Cosmo Bio Co. Ltd (Toyo 2Chome, Koto-Ku, Tokyo 135-0016, Japan; product No. SML-ROKO2-EX). An alternative method is determination of ascorbic acid content in plant extract using the Reflectoquant® Ascorbic acid test, wherein ascorbic acid reduces yellow molybdophosphoric acid to phosphomolybdenum blue, the concentration of which is determined reflectometrically. Reflectoquant® ascorbic acid test strips and a reading apparatus (RQflex 10) are commercially available e.g. from Merck Company.

Linear regression analysis is a well-known method in the art. It may be advisable to eliminate data points that clearly are lying outside of the regression (i.e. outside of the 90% confidence interval) or data points which would have to high weight (e.g. are far away from the other data points) prior to determining the slope of the linear curve as the ascorbate profile value.

To mitigate the influence of environmental and other factors which may have an impact on the absolute values of ascorbate concentration, content as well as on the ascorbate profile value determined in different experiments and result in fluctuations between experiments, it may be beneficial to include a reference plant line into the experimental set-up.

Thus, the invention also provides a method for determining the "relative ascorbate profile value" of a test plant line compared to a reference plant line comprising the steps of
 a. growing several seedlings of test plant line for a time period sufficient to generate a population of seedlings with smaller and larger cotyledons (or other plant parts as described herein) and growing several seedlings of a reference plant line from the same plant species for the same time period;
 b. determining the weight of the individual cotyledons (or other plant parts) and measuring the concentration of ascorbate in the individual cotyledons (or other plant parts) for the test plant line and for the reference plant line;
 c. plotting the concentration of ascorbate versus the weight of each individual cotyledon for the test plant line and for the reference plant line;
 d. performing regression analysis on the data points to obtain a linear regression curve for the test plant line and for the reference plant line;
 e. determining the slope of the regression line for the test plant line, which corresponds to the ascorbate profile value of the test plant line and determining the slope of the regression line for the reference plant line, which corresponds to the ascorbate profile value of the reference plant line; and
 f. dividing the value for the ascorbate profile value of the test plant line by the value for the ascorbate profile value of the reference plant line to obtain the relative ascorbate profile value The relative ascorbate profile value may now be used to compare ascorbate profiles of plant lines determined in different experimental set-ups to make the values comparable, and the comparison meaningful.

If the reference plant line is a plant line with a known yield potential or shelf life, the relative ascorbate profile value ("RAPV') will indicate whether the test plant line has a higher yield potential or shelf life (RAPV>1) or a lower yield potential or shelf life (RAPV<1). The more the RAPV differs from 1, the bigger the difference in yield potential or shelf life between the test plant line and the reference plant line.

The relative ascorbate profile value may also be used to rank plant lines in a population of plant lines and select only those plant lines which are of interest. E.g. only the better performing lines, i.e. the plant lines with the highest predicted yield potential or the longest predicted shelf life may be included in field trial programs, thus allowing to make a better use of time and resources. In other instances, the predictive value of the relative ascorbate profile value may be used to eliminate the predicted poor performing lines from a breeding program.

The invention thus also provides a method for breeding plants comprising the steps of
 a. generating a breeding population of plant lines;
 b. determining the relative ascorbate profile value for each of said plant lines of said population compared to a reference plant line by the method according to the invention;
 c. selecting one or more plant lines with the highest relative ascorbate profile value(s);
 d. crossing said selected plant lines with other plants to generate a further breeding population; and
 e. optionally reiterating the process through steps b to d.

In another aspect of the invention, a method for selecting parental lines in hybrid plant production is provided which comprising the steps of
 a. providing a population of at least two parental plant lines;
 b. crossing different combinations of parental plant lines selected from said population to generate hybrid plant lines;
 c. determining the relative ascorbate profile value for said hybrid plant lines according to the method of the invention;
 d. selecting parental lines which yield hybrid plant lines with the highest ascorbate profile value.

As used herein unless clearly indicated otherwise, the term "plant" intends to mean a plant at any developmental stage. Moreover, the term also encompasses "parts of a plant". The term "plant" encompasses a plant as described herein, or progeny of the plants which retain the distinguishing characteristics of the parents, such as seed obtained by selfing or crossing, e.g. hybrid seed (obtained by crossing two inbred parental lines), hybrid plants and plant parts derived there from are encompassed herein, unless otherwise indicated.

"Parts of (a) plant(s)" may be attached to or separate from a whole intact plant. Such parts of a plant include, but are not limited to, cells of a plant, tissues or organs, seeds, severed parts such as roots, leaves, flowers, pollen, fruits, etc.

The methods of the invention are very well suited for Brassicaceae plants, particularly oilseed rape, but may be used to similar ends in other plants such as lettuce, tobacco, cotton, corn, rice, wheat, vegetable plants, carrot, cucumber, leek, pea, melon, potato, tomato, sorghum, rye, oat, sugarcane, peanut, flax, bean, sugar beets, soya, sunflower, ornamental plants.

The invention also relates to plant line with a relative ascorbate profile value of more than one when compared to the best reference plant line of that plant species. Also provided are *Brassica* plant lines with an ascorbate profile value of more than 330.

It must be noted that as used herein, the terms "a", "an", and "the", include singular and plural references unless the context clearly indicates otherwise, i.e., such terms may refer to "one", "one or more" or "at least one". Thus, for example, reference to "a reagent" includes one or more of such different reagents and reference to "the method" includes reference to equivalent steps and methods known to those of ordinary skill in the art that could be modified or substituted for the methods described herein.

All publications and patents cited in this disclosure are incorporated by reference in their entirety. To the extent the material incorporated by reference contradicts or is inconsistent with this specification, the specification will supersede any such material.

A "plant line" as used herein is collection of plants distinguishable from other similar collections of plants, wherein the individual plants within the population are genetically similar. A plant line may be obtained using conventional breeding techniques including crossing and selection, or may also be obtained by transformation with a particular DNA construct. In the latter case the individual transformants usually constitute plant lines. Plant lines may also be so-called doubled haploids, wherein plants are generated from haploid (or uneven-ploid) cell types (usually microspores or pollen) and treated to double the chromosomes to obtain a diploid (or even-ploid) plant. Plant lines may also be varieties as defined under the UPOV convention.

A "breeding population" as used herein is a collection of plant lines obtained by initially crossing two or more parent lines, to generate a collection of plant lines wherein the plant lines differ from each other in their genetic composition. A breeding population may be a collection of double haploid lines.

As used herein, a "*Brassica* plant" is a plant which belongs to one of the species *Brassica napus, Brassica rapa* (or *campestris*), or *Brassica juncea*. Alternatively, the plant can belong to a species originating from intercrossing of these *Brassica* species, such as *B. napocampestris*, or of an artificial crossing of one of these *Brassica* species with another species of the *Cruciferacea*. As used herein "oilseed plant" refers to any one of the species *Brassica napus, Brassica rapa* (or *campestris*), *Brassica carinata, Brassica nigra* or *Brassica juncea*.

"Cotton" as used herein includes *Gossypium hirsutum* or *Gossypium barbadense*.

The term "wheat plant" as herein used means plant species of the genus *Triticum* or plants resulting from crosses with plants of the genus *Triticum*, particularly plant species of the genus *Triticum* or plants resulting from crosses with plants of the genus *Triticum*, which are used in agriculture for commercial purposes, and particularly preferably *Triticum aestivum* or *Triticum durum*. Plants obtained from such a cross include triticale plants.

In conjunction with the present invention, the term "rice plant" means plant species of the genus *Oryza*, particularly *Oryza sativa*, preferably japonica, indica or javanica rice, whether soil, water, upland, rainfed shallow, deep water, floating or irrigated rice.

"Maize plant" as herein used refers to a plant of the species of the genus *Zea*, particularly plant species of the genus *Zea*, which are used in agriculture for commercial purposes including *Zea mays*.

As used herein "comprising" is to be interpreted as specifying the presence of the stated features, integers, steps or components as referred to, but does not preclude the presence or addition of one or more features, integers, steps or components, or groups thereof.

Recombinant DNA techniques or molecular analyses if needed may be carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

EXAMPLES

Example 1: Determination of Ascorbate Profile Values for *Brassica napus* Lines and Hybrids The ascorbate profile value of a population of plants is determined according to the following outline:
  growing the seedlings until a population of seedlings is obtained with smaller and larger cotyledons (possible very first stage of senescence in larger cotyledons as determined biochemically or molecularly, but no visible symptoms yet)
  optionally, apply moderate stress before harvesting the cotyledons
  determining the weight of the cotyledons
  measuring the concentration of ascorbate in the cotyledons
  Calculating the slope of the linear regression curve for data points wherein the ascorbate concentration in mg/L is the plotted on the y-axis and the weight of cotyledon is plotted on the x-axis.

About 18 to 20 seeds of a *Brassica napus* plant line or hybrid line are grown individually in Jiffy 7C pots (Jiffy Products International B.V., The Netherlands) (one seed/Jiffy). It is advisable to include a control or reference line for calibration between experiments. The seedlings are grown for 12 days in growth room with the following conditions: 16 hours light/8 hours dark; 21° C. day/19° C. night. To minimize fluctuations in growth conditions, the Jiffy pots are regularly rotated according to a predetermined scheme, and watered in accordance with Table 2.

Cotyledons are harvested at day 12, during the day, after at least a few hours of light, usually after 6 hours of light. It has been experimentally determined, that thereafter, the ascorbate profile value does not change significantly during the rest of the light period. The cotyledons are individually weighed and put in Lysing Matrix A tubes from MP Biomedicals (Illkirch, France) and frozen immediately in liquid nitrogen.

The samples are crushed with the 'Fast prep-24' from MP Biomedicals (2 times 20 seconds) and the supernatants are transferred to a new container. The concentration of ascorbic acid is measured using the 'Vitamin C Assay Kit' according to the manufacturer's instructions (Cosmo Bio Co., Ltd Japan) or via the Refletoquant Ascorbic acid test according to the manufacturer's instructions (Merck).

TABLE 2

Watering and rotating scheme of trays

| Day after sowing | Watering | Rotating |
|---|---|---|
| 0 (sowing) | Saturate Jiffy's | |
| 1 | | |
| 2 | 600 mL | + |
| 3 | | |
| 4 | 600 mL | + |
| 5 | | |
| 6 | 400-500 mL | + |
| 7 | 400 mL | + |
| 8 | | |
| 9 | 600 mL | + |
| 10 | | |
| 11 | Optionally 600 mL | + |
| 12 (harvest) | | |

The data are next plotted in a graph (see FIG. 1) wherein on the y-axis the ascorbate concentration of an individual cotyledon is indicated and on the x-axis the weight of that cotyledon. A regression analysis to obtain a linear regression curve of the form y=ax+b is performed. The most aberrant values (outside of the 90% confidence interval) are preferably eliminated and slope and Pearson correlation are recalculated (preferably the Pearson correlation is more than 0.70).

Example 2: Correlation of the Relative Ascorbate Profile Value with Yield Determination in *Brassica napus* Hybrids The method described in Example 1 was used to determine the ascorbate profile values for about 21 *Brassica napus* hybrids as well as for a control hybrid line, which preferably but not necessarily has a similar genetic background, and importantly for which well characterized yield data are available. The determined ascorbate profile values were standardized by dividing these value by the ascorbate profile value determined for the reference control line.

These 21 *Brassica napus* hybrids were also subjected to field trials (default on 5 locations, 3 repetitions per location on plots of 10 m$^2$) to determine their yield potential. The yield as determined by the field trials was expressed as a score from 1 to 9, whereby 1 represents the highest yield, and 9 represents the lowest yield. The results are summarized in table 3.

TABLE 3

| Hybrid | Relative ascorbate profile value | Yield Score |
|---|---|---|
| Line 23 | 1.520 | 1 |
| Line 22 | 1.321 | 2 |
| Line 20 | 1.228 | 3.1 |
| Line 21 | 1.220 | 3.3 |
| Line 13 | 1.186 | 3.2 |
| Line 8 | 1.158 | 3.4 |
| Line 14 | 1.096 | 3.5 |
| Line 17 | 1.057 | 4.1 |
| Line 18 | 1.053 | 4.3 |
| Line 7 | 0.990 | 4.5 |
| Line 16 | 0.953 | 4.2 |
| Line 19 | 0.953 | 4.6 |
| Line 15 | 0.913 | 4.4 |
| Line 1 | 0.910 | 4.8 |
| Line 2 | 0.893 | 4.7 |
| Line 6 | 0.890 | 8 |
| Line 4 | 0.884 | 9 |
| Line 9 | 0.871 | 5 |
| Line 10 | 0.787 | 7 |
| Line 3 | 0.675 | 6 |

Figure 3:
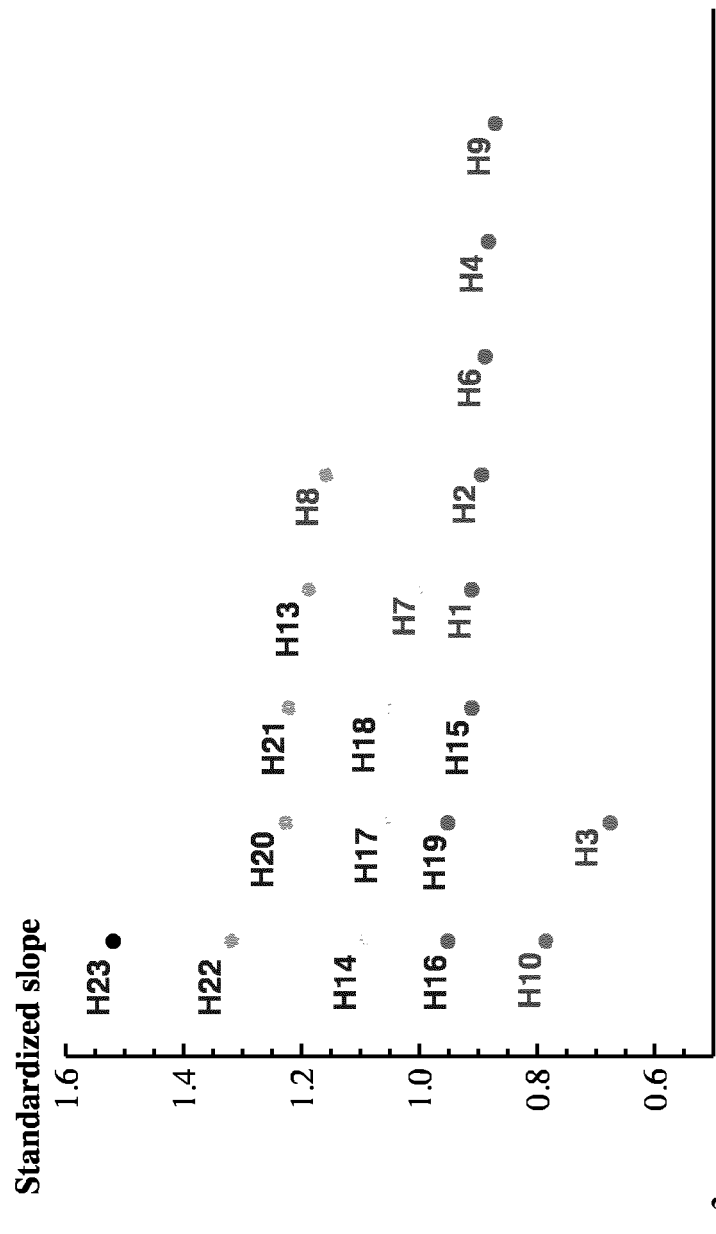
FIG. 3 depicts a clustering of the different *B. napus* hybrids by their standardized ascorbate profile values as shown in Table 3.
Figure 4:
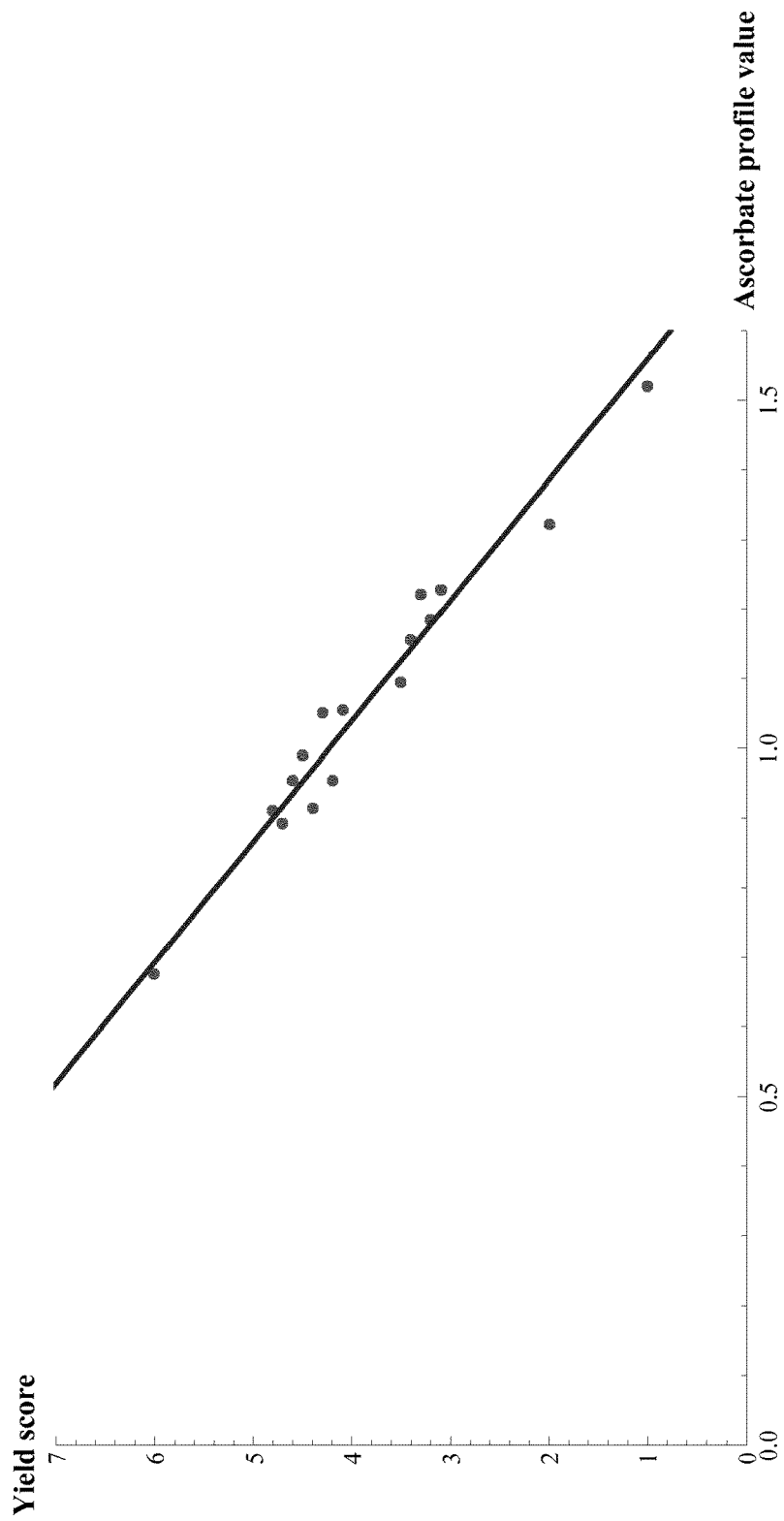
FIG. 4 is a schematic representation of the standardized ascorbate profile values determined for different *B. napus* hybrids plotted versus their yield score determined in field trials. X-axis: relative ascorbate profile value; Y-axis: yield-score.

When clustering the standardized ascorbate profile values (FIG. 3) or performing a regression analysis (FIG. 4) it becomes apparent that the highest yielding hybrid lines also have the highest (relative) ascorbate profile values. Moreover, up to and including yield score class 5, the Pearson correlation between the yield score and the relative ascorbate profile value is 0.97. The herein described methods can thus be used to divide the population of hybrid lines into the best performing ones, the intermediate performing ones and the low performing lines.

Clustering data points can be performed e.g. using software packages available in the art, such as Wolfram Mathematica 8 (Wolfram Research, Inc. Champaign, Ill., USA).

Example 3: Determination of Ascorbate Profile Values for Lettuce Varieties

The ascorbate profile value for lettuce varieties was determined in a similar way as described in Example 1. Seeds of lettuce lines were pregerminated on wet filter paper and sown in Jiffy 7C pots. About 35 seedlings are needed to determine the ascorbate profile value. The seedlings are grown for 10 days in growth room with the following conditions: 16 hours light/8 hours dark; 21° C. day/19° C. night. To minimize fluctuations in growth conditions, the Jiffy pots are regularly rotated according to a predetermined scheme, and watered in accordance with Table 4.

TABLE 4

Watering and rotating scheme of trays

| Day after sowing | Watering | Rotating |
|---|---|---|
| 0 (sowing) | Saturate Jiffy's | |
| 1 | | |
| 2 | 600 mL | + |
| 3 | | |
| 4 | 600 mL | + |
| 5 | | |
| 6 | 600 mL | + |
| 7 | | |
| 8 | 600 mL | + |
| 9 | | |
| 10 (harvest) | | |

Cotyledons are harvested at day 10, during the day, after at least a few hours of light, usually after 6 hours of light.

The cotyledons are individually weighed and put in Lysing Matrix A tubes from MP Biomedicals (Illkirch, France) and frozen immediately in liquid nitrogen.

The samples are crushed with the 'Fast prep-24' from MP Biomedicals (2 times 20 seconds) and the supernatants are transferred to a new container. The concentration of ascorbic acid is measured using the 'Vitamin C Assay Kit' according to the manufacturer's instructions (Cosmo Bio Co., Ltd Japan).

The data are next plotted in a graph wherein on the y-axis the ascorbate concentration of an individual cotyledon is indicated and on the x-axis the weight of that cotyledon. A regression analysis to obtain a linear regression curve of the form y=ax+b is performed. The most aberrant values (outside of the 90% confidence interval) are preferably eliminated and slope and Pearson correlation are recalculated (preferably the Pearson correlation is more than 0.70).

Example 4: Determination of Ascorbate Profile Values for Wheat Lines

The ascorbate profile value for wheat lines was determined in a similar way as described in Example 1, except that the analysis was performed on the first true leaf.

About 35 seeds per line are sown in pots (width 9-height 10 cm) containing potting soil for sowing and grafting, and some fertilizer. 4 seeds are sown per pot. The seedlings are grown for about 11-12 days in growth room with the following conditions: 16 hours light/8 hours dark; 200 µmol $m^{-2}$ $sec^{-1}$; 24° C. day/20° C. night; humidity 60%. To minimize fluctuations in growth conditions, the pots are regularly rotated according to a predetermined scheme and watered regularly.

The first true leaves are harvested at day 11-12, during the day, after at least a few hours of light, usually after 6 hours of light. The samples are individually weighed and put in Lysing Matrix A tubes from MP Biomedicals (Illkirch, France) and frozen immediately in liquid nitrogen.

The samples are crushed with the 'Fast prep-24' from MP Biomedicals (2 times 20 seconds) and the supernatants are transferred to a new container. The concentration of ascorbic acid is measured using the 'Vitamin C Assay Kit' according to the manufacturer's instructions (Cosmo Bio Co., Ltd Japan) or via the Refletoquant Ascorbic acid test according to the manufacturer's instructions (Merck).

The data are next plotted in a graph wherein on the y-axis the ascorbate concentration of an individual cotyledon is indicated and on the x-axis the weight of that cotyledon. A regression analysis to obtain a linear regression curve of the form y=ax+b is performed. The most aberrant values (outside of the 90% confidence interval) are preferably eliminated and slope and Pearson correlation are recalculated (preferably the Pearson correlation is more than 0.70).

Example 5: Determination of Ascorbate Profile Values for Rice Lines

The ascorbate profile value for rice lines was determined in a similar way as described in Example 1, except that the analysis was performed on the second true leaf.

Rice seeds are pregerminated on wet filter paper and about 35 seeds per line are sown in pots (width 9-height 10 cm) containing potting soil for sowing and grafting, and some fertilizer. 4 seeds are sown per pot. The seedlings are grown for about 17 days in growth room with the following conditions: 16 hours light/8 hours dark; 300 µmol m-2 sec-1; 26° C. day/21° C. night; humidity 71%. To minimize fluctuations in growth conditions, the pots are regularly rotated according to a predetermined scheme and watered regularly so that the trays always contain water.

The second leaves are harvested at day 17, during the day, after at least a few hours of light, usually after 6 hours of light. The samples are individually weighed and put in Lysing Matrix A tubes from MP Biomedicals (Illkirch, France) and frozen immediately in liquid nitrogen.

The samples are crushed with the 'Fast prep-24' from MP Biomedicals (2 times 20 seconds) and the supernatants are transferred to a new container. The concentration of ascorbic acid is measured using the 'Vitamin C Assay Kit' according to the manufacturer's instructions (Cosmo Bio Co., Ltd Japan) or via the Refletoquant Ascorbic acid test according to the manufacturer's instructions (Merck).

The data are next plotted in a graph wherein on the y-axis the ascorbate concentration of an individual cotyledon is indicated and on the x-axis the weight of that cotyledon. A regression analysis to obtain a linear regression curve of the form y=ax+b is performed. The most aberrant values (outside of the 90% confidence interval) are preferably eliminated and slope and Pearson correlation are recalculated (preferably the Pearson correlation is more than 0.70).

The invention claimed is:

1. A method for breeding plants comprising the step of
   a. generating a breeding population of plant lines;
   b. determining the relative ascorbate profile value for each of said plant lines of said population compared to a reference plant line by a method for determining the relative ascorbate profile value of a test plant line compared to a reference plant line grown comprising the steps of:
      (i) determining the ascorbate profile value for a test plant line and for a reference plant line grown under similar conditions according to a method for determining the ascorbate profile value of a plant line comprising the steps of:
         growing several seedlings of said plant line for a time sufficient to generate a population of seedlings wherein at least one plant part does not develop any further;
         determining the weight of the individual plant parts and measuring the concentration of ascorbate in said individual plant parts;
         plotting the concentration of ascorbate versus the weight determined for each individual plant to obtain a collection of data points;
         performing regression analysis on the data points to obtain a linear regression curve; and
         determining the slope of the linear regression curve, which corresponds to the ascorbate profile value of the plant line; and
      (ii) dividing the ascorbate profile value of the test plant line by the ascorbate profile value of the reference plant line to obtain the relative ascorbate profile value;
   c. selecting one or more plant lines with the highest relative ascorbate profile value(s);
   d. crossing said selected plant lines with other plants to generate a further breeding population; and
   e. optionally reiterating the process through steps b to d.

2. A method for selecting parental lines in hybrid plant production comprising the steps of
   a. providing a population of at least two parental plant lines;

b. crossing different combinations of parental plant lines selected from said population to generate hybrid plant lines;

c. determining the relative ascorbate profile value for said hybrid plant lines according to a method for determining the relative ascorbate profile value of a test plant line compared to a reference plant line grown comprising the steps of:

(i) determining the ascorbate profile value for a test plant line and for a reference plant line grown under similar conditions according to a method for determining the ascorbate profile value of a plant line comprising the steps of:

growing several seedlings of said plant line for a time sufficient to generate a population of seedlings wherein at least one plant part does not develop any further;

determining the weight of the individual plant parts and measuring the concentration of ascorbate in said individual plant parts;

plotting the concentration of ascorbate versus the weight determined for each individual plant to obtain a collection of data points;

performing regression analysis on the data points to obtain a linear regression curve; and determining the slope of the linear regression curve, which corresponds to the ascorbate profile value of the plant line; and (ii) dividing the ascorbate profile value of the test plant line by the ascorbate profile value of the reference plant line to obtain the relative ascorbate profile value;

d. selecting parental lines which yield hybrid plant lines with the highest ascorbate profile value.

3. The method of claim 2, comprising an additional step of applying moderate stress prior to the step of determining the weight and ascorbate concentration in said individual plant parts, wherein said moderate stress is moderate drought stress.

4. The method of claim 2, wherein said seedlings are grown until the plant part, which does not develop any further, starts to demonstrate symptoms of senescence as determined biochemically or molecularly, without visible symptoms of senescence.

5. The method of claim 2, wherein said plant part which does not develop any further is a cotyledon or an epicotyl.

6. The method of claim 2, wherein said plant part which does not develop any further is the first or second developing true leaf.

7. The method of claim 2, wherein said ascorbate concentration is measured by specific light absorption of the dinitrophenylhydrazine derivative of oxidized ascorbic acid, or by measuring the reduction of yellow molybdophosphoric acid to phosphomolybdenum blue by ascorbic acid reflectometrically.

8. The method of claim 2, wherein said plant is selected from oilseed rape, lettuce, tobacco, cotton, corn, rice, wheat, vegetable plants, carrot, cucumber, leek, pea, melon, potato, tomato, sorghum, rye, oat, sugarcane, peanut, flax, bean, sugar beets, soya, sunflower, ornamental plants.

9. The method of claim 1, comprising an additional step of applying moderate stress prior to the step of determining the weight and ascorbate concentration in said individual plant parts, wherein said moderate stress is moderate drought stress.

10. The method of claim 1, wherein said seedlings are grown until the plant part, which does not develop any further, starts to demonstrate symptoms of senescence as determined biochemically or molecularly, without visible symptoms of senescence.

11. The method of claim 1, wherein said plant part which does not develop any further is a cotyledon or an epicotyl.

12. The method of claim 1, wherein said plant part which does not develop any further is the first or second developing true leaf.

13. The method of claim 1, wherein said ascorbate concentration is measured by specific light absorption of the dinitrophenylhydrazine derivative of oxidized ascorbic acid, or by measuring the reduction of yellow molybdophosphoric acid to phosphomolybdenum blue by ascorbic acid reflectometrically.

14. The method of claim 1, wherein said plant is selected from oilseed rape, lettuce, tobacco, cotton, corn, rice, wheat, vegetable plants, carrot, cucumber, leek, pea, melon, potato, tomato, sorghum, rye, oat, sugarcane, peanut, flax, bean, sugar beets, soya, sunflower, ornamental plants.

* * * * *